US012697495B2

(12) United States Patent
Hussein et al.

(10) Patent No.: US 12,697,495 B2
(45) Date of Patent: Aug. 4, 2026

(54) IMPLANTABLE MEDICAL DEVICE WITH CORROSION-RESISTANT FEEDTHROUGH ASSEMBLY

(71) Applicant: Pacesetter, Inc., Sylmar, CA (US)

(72) Inventors: Haytham Hussein, Greer, SC (US); John Szymanski, Santa Clarita, CA (US); Kavous Sahabi, Winnetka, CA (US); Ofer Rosenzweig, West Hills, CA (US); Stella Nichols, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 967 days.

(21) Appl. No.: 17/356,397

(22) Filed: Jun. 23, 2021

(65) Prior Publication Data

US 2022/0409909 A1 Dec. 29, 2022

(51) Int. Cl.
| | |
|---|---|
| *A61N 1/375* | (2006.01) |
| *H01M 50/186* | (2021.01) |
| *H01M 50/191* | (2021.01) |
| *H01M 50/198* | (2021.01) |

(52) U.S. Cl.
CPC ....... *A61N 1/3754* (2013.01); *A61N 1/37512* (2017.08); *H01M 50/186* (2021.01); *H01M 50/191* (2021.01); *H01M 50/198* (2021.01)

(58) Field of Classification Search
CPC ............. A61N 1/3754; A61N 1/37512; H01M 50/186; H01M 50/191; H01M 50/198; H01M 50/247; H01M 2220/30
See application file for complete search history.

(56) References Cited

U.S. PATENT DOCUMENTS

| | | | |
|---|---|---|---|
| 6,622,046 B2 † | 9/2003 | Fraley | |
| 6,765,779 B2 † | 7/2004 | Stevenson | |
| 6,768,629 B1 † | 7/2004 | Allen | |
| 8,175,700 B2 † | 5/2012 | Johnson | |
| 8,660,645 B2 † | 2/2014 | Stevenson | |
| 10,874,865 B2 † | 12/2020 | Dollar | |

(Continued)

FOREIGN PATENT DOCUMENTS

| | | | | |
|---|---|---|---|---|
| CA | 1279694 C | * | 1/1991 | ........... H01B 17/305 |
| GB | 1562915 A | * | 3/1980 | ........... A61N 1/3754 |

OTHER PUBLICATIONS

May, Clayton A. Epoxy Resins: Chemistry and Technology. 2nd ed. 1988. (Year: 1988).*

*Primary Examiner* — Jennifer Pitrak McDonald
*Assistant Examiner* — Christine Sison
(74) *Attorney, Agent, or Firm* — Dean D. Small; Carroll, Hoette & Butscher, LLC

(57) ABSTRACT

A feedthrough assembly for an implantable medical device includes a housing, a solid insert, one or more conductive elements, a metal filler, and a non-corrosive sealant. The housing defines a central cavity through a height of the housing. The solid insert is disposed within the central cavity of the housing. The one or more conductive elements extend through one or more apertures defined within the solid insert and extend through the central cavity of the housing. The metal filler is disposed within a joint defined by an outer surface of the solid insert and an inner surface of the housing that defines the central cavity. The non-corrosive sealant coats a top surface of the metal filler to inhibit corrosion of the metal filler.

21 Claims, 8 Drawing Sheets

(56)                    References Cited

U.S. PATENT DOCUMENTS

| | | | |
|---|---|---|---|
| 2003/0179536 A1* | 9/2003 | Stevenson | H01G 4/35 |
| | | | 361/302 |
| 2017/0294250 A1* | 10/2017 | Giese | A61N 1/3754 |
| 2019/0134407 A1* | 5/2019 | Dollar | H01G 4/224 |
| 2019/0232066 A1* | 8/2019 | Lim | A61N 1/3754 |

\* cited by examiner

† cited by third party

IMPLANTABLE MEDICAL DEVICE WITH CORROSION-RESISTANT FEEDTHROUGH ASSEMBLY

BACKGROUND

Embodiments of the present disclosure generally relate to implantable medical devices and methods, and more particularly to implantable medical devices having feedthrough assemblies.

Implantable medical devices (IMDs), particularly those used for cardiac rhythm management and neuromodulation applications, are manufactured to have a feedthrough assembly that connects the electronics contained within a hermetically sealed enclosure to the components responsible for delivering therapy to the patient. A critical function of the feedthrough assembly is to maintain hermeticity of the device case.

With the increased miniaturization of IMDs, there is an increased likelihood that the feedthrough assembly will be exposed to electrolyte solutions such as body fluid. These interactions may produce unwanted electrochemical reactions thereby compromising the integrity of the feedthrough and IMD. Such reactions can interfere with the functionality of the IMD and shorten its operational lifespan. A need therefore remains for a feedthrough assembly of an IMD (e.g., a pacemaker, insertable cardiac monitor, or implantable neurostimulator device) to have enhanced corrosion resistance in the presence of an electrolyte solution (e.g. body fluid) to sustain the hermeticity and maximize the operational lifespan of the IMD.

SUMMARY

In one or more embodiments, a feedthrough assembly for an implantable medical device is provided. The feedthrough assembly includes a housing, a solid insert, one or more conductive elements, a metal filler, and a non-corrosive sealant. The housing defines a central cavity through a height of the housing. The solid insert is disposed within the central cavity of the housing. The one or more conductive elements extend through one or more apertures defined within the solid insert and extend through the central cavity of the housing. The metal filler is disposed within a joint defined by an outer surface of the solid insert and an inner surface of the housing that defines the central cavity. The non-corrosive sealant coats a top surface of the metal filler to inhibit corrosion of the metal filler.

Optionally, the non-corrosive sealant is electrically insulative. The non-corrosive sealant may include alumina, parylene, polyurethane, silicone, and/or an epoxy material. Alternatively, the non-corrosive sealant is electrically conductive. The metal filler may include gold.

Optionally, the non-corrosive sealant coats at least a majority of a top surface of the solid insert. The non-corrosive sealant individually surrounds each of the one or more conductive elements along a segment of the respective conductive element that protrudes beyond the top surface of the solid insert. Optionally, the housing has a raised lip that projects from a top surface of the housing and extends along an outer perimeter of the housing. The raised lip defines an outer edge of a well that encompasses the joint and the metal filler. The non-corrosive sealant at least partially fills the well to coat the metal filler.

Optionally, the non-corrosive sealant is a bead that extends along the joint without covering a majority of a top surface of the solid insert or a majority of a top surface of the housing.

Optionally, the housing comprises a metal material and the solid insert comprises a ceramic material. The housing may include titanium. The housing may have protrusions along an outer perimeter of the housing for coupling to a header of the implantable medical device. The one or more conductive elements may be configured to electrically connect to an antenna and/or a sensing electrode held in the header.

Optionally, the central cavity of the housing is elongated along an axis orthogonal to the height of the housing, and the one or more conductive elements include multiple conductive elements arranged in a line along the axis.

In one or more embodiments, a method of producing a feedthrough assembly is provided. The method includes installing a solid insert within a central cavity of a housing. The central cavity extends through a height of the housing. The method includes installing one or more conductive elements through one or more apertures defined within the solid insert, and depositing a metal filler within a joint defined by an outer surface of the solid insert and an inner surface of the housing that defines the central cavity. The method also includes coating a top surface of the metal filler with a non-corrosive sealant to inhibit corrosion of the metal filler.

Optionally, the non-corrosive sealant is coated on the top surface of the metal filler via one of chemical vapor deposition, physical vapor deposition, injection molding, precision fluid dispensing, or casting. Optionally, the non-corrosive sealant includes alumina, parylene, polyurethane, silicone, and/or an epoxy material, the solid insert includes a ceramic material, and the housing includes a metal material.

Optionally, the non-corrosive sealant is coated on the top surface of the metal filler to also coat at least a majority of a top surface of the solid insert. The non-corrosive sealant individually surrounds each of the one or more conductive elements along a segment of the respective conductive element that protrudes beyond the top surface of the solid insert.

Optionally, the housing has a raised lip that projects from a top surface of the housing and extends along an outer perimeter of the housing. The raised lip defines an outer edge of a well that encompasses the joint and the metal filler. The non-corrosive sealant is coated on the top surface of the metal filler by at least partially filling the well with the non-corrosive sealant.

Optionally, the non-corrosive sealant is coated on the top surface of the metal filler by applying a bead of the non-corrosive sealant along a full length of the joint without covering a majority of a top surface of the solid insert or a majority of a top surface of the housing with the non-corrosive sealant.

In one or more embodiments, an implantable medical device is provided that includes a header and a feedthrough assembly. The header includes a header body, an antenna, and a sensing electrode. The antenna and the sensing electrode are both disposed within the header body. The feedthrough assembly is mounted to a mounting end of the header body. The feedthrough assembly includes a housing, a solid insert, conductive elements, a metal filler, and a non-corrosive sealant. The housing defines a central cavity through a height of the housing. The solid insert is disposed within the central cavity of the housing. The conductive elements extend through apertures defined within the solid insert and extend through the central cavity of the housing. A first conductive element of the conductive elements is electrically connected to the antenna, and a second conductive element of the conductive elements is electrically connected to the sensing electrode. The metal filler is disposed within the apertures between the corresponding conductive elements within the apertures and the solid insert to seal the apertures. The non-corrosive sealant coats a top surface of the metal filler to inhibit corrosion of the metal filler. The header body couples to the housing of the feedthrough assembly and envelops the non-corrosive sealant.

Optionally, the implantable medical device also includes a case that encloses a battery and an electronics module within an internal cavity of the case. The feedthrough assembly is disposed between the header and the case, and the conductive elements of the feedthrough assembly project into the internal cavity and electrically connect to the battery and the electronics module. The feedthrough assembly maintains hermeticity of the case.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Embodiments may be implemented in connection with one or more implantable medical devices (IMDs). Non-limiting examples of IMDs include neurostimulator devices, implantable leadless monitoring and/or therapy devices, and alternative implantable medical devices. For example, an IMD may represent a cardiac monitoring device, a leadless pacemaker, a cardioverter, a cardiac rhythm management device, a defibrillator, a neurostimulator, or the like.

Figure 1:
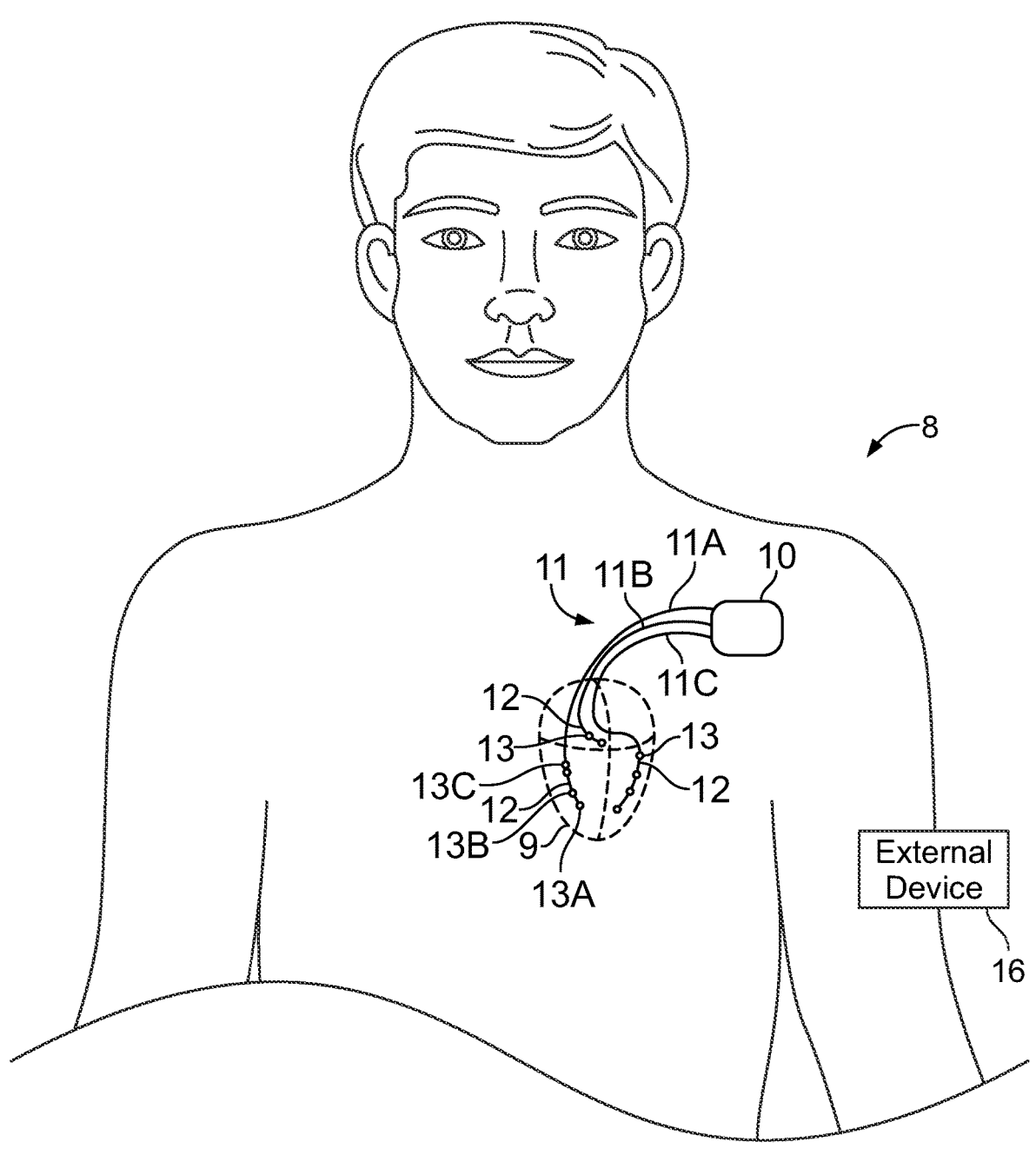
FIG. 1 illustrates an implantable medical device (IMD) coupled to a heart in a patient in accordance with one embodiment.

FIG. 1 illustrates an implantable medical device (IMD) 8 coupled to a heart 9 in a patient in accordance with one embodiment. The IMD 8 may be configured to both monitor the heart 9 and provide stimulation therapy to the heart 9. The IMD 8 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. The IMD 8 may be controlled to sense atrial and ventricular waveforms of interest, discriminate between two or more ventricular waveforms of interest, deliver stimulation pulses for pacing and/or shocks, and inhibit application of a stimulation pulse to a heart based on the discrimination between the waveforms of interest and the like.

The IMD 8 includes a device case or housing 10 that is connected to at least one lead 11. The leads 11 are cardiac leads that extend from the case 10 to the heart 9 of the patient. A proximal end of each lead is connected to the case 10, and a distal end of each lead is in contact with patient tissue within the heart 9 or surrounding the heart 9. Three leads 11 are shown in FIG. 1, but the IMD 8 may include more or less than three leads in another embodiment.

The leads 11 measure cardiac signals of the heart 9 and may also deliver stimulation therapy to the heart 9. For example, the leads 11 may detect intracardiac electrogram (IEGM) signals that form an electrical activity indicator of myocardial function over multiple cardiac cycles of the heart 9. The leads 11 may include a right ventricular lead 11A, a right atrial lead 11B, and a coronary sinus lead 11C. Each lead 11 includes a respective lead body 12 and at least one electrode 13. The leads 11 in the illustrated embodiment have multiple electrodes 13. The electrodes 13 may deliver electrical stimulation or pulses to the patient tissue in contact with the electrodes 13. The electrode 13 may also sense to receive cardiac signals (e.g., IEGM signals) from the heart 9. In an embodiment, a single electrode 13 may emit a stimulation pulse in a stimulation mode, and then may quickly switch to a monitoring mode to detect cardiac signals following the stimulation pulse.

The electrodes 13 may include a tip electrode 13A, a ring electrode 13B, a coil electrode 13C, and/or the like. On the right ventricular lead 11A, the tip electrode 13A is located at the distal end of the lead 11A, opposite the end extending from the case 10. The ring electrode 13B and the coil electrode 13C of the lead 11A are disposed between the tip electrode 13A and the case 10 along the length of the lead 11A, although are closer to the tip electrode 13A than to the case 10. The tip electrode 13A is separated from the ring electrode 13B by a length of the lead body 12. The ring electrode 13B is separated from the coil electrode 13C by another length of the lead body 12.

The case 10 may contain a battery, pulse generation circuitry, communication circuitry, a data storage device (e.g., memory), and/or control circuitry. The control circuitry is for receiving and analyzing electrocardiogram IEGM signals from the electrodes 13. The control circuitry may include at least one processor for processing the IEGM signals in accordance with algorithms to make determinations about the state of the heart 9. The memory provides storage for the cardiac signals and programmed instructions for the control circuitry. The battery powers the circuitry with the case 10. For example, the battery powers the pulse generation circuitry to generate stimulation pulses and powers the communication circuitry to communicate with an external device 16. The control circuitry may generate messages to be communicated via the communication circuitry to the external device 16. The messages may include the IEGM signals and/or data generated based on the IEGM signals.

The external device 16 may represent a portable smartphone, tablet device, bedside monitor installed in a patient's home, or the like. The external device 16 may be a programmer device used in the clinic to interrogate the IMD 8, retrieve data and program detection criteria and other features. The external device 16 facilitates access by physicians to patient data as well as permits the physician to review real-time electrocardiogram (ECG) signals while being collected by the IMD 8.

Although one or more embodiments described herein are directed to IMDs with leads, one or more of the embodiments can be applied to leadless IMDs, such as a leadless pacemaker, neurostimulation device, pressure sensor, or the like.

Figure 2A:
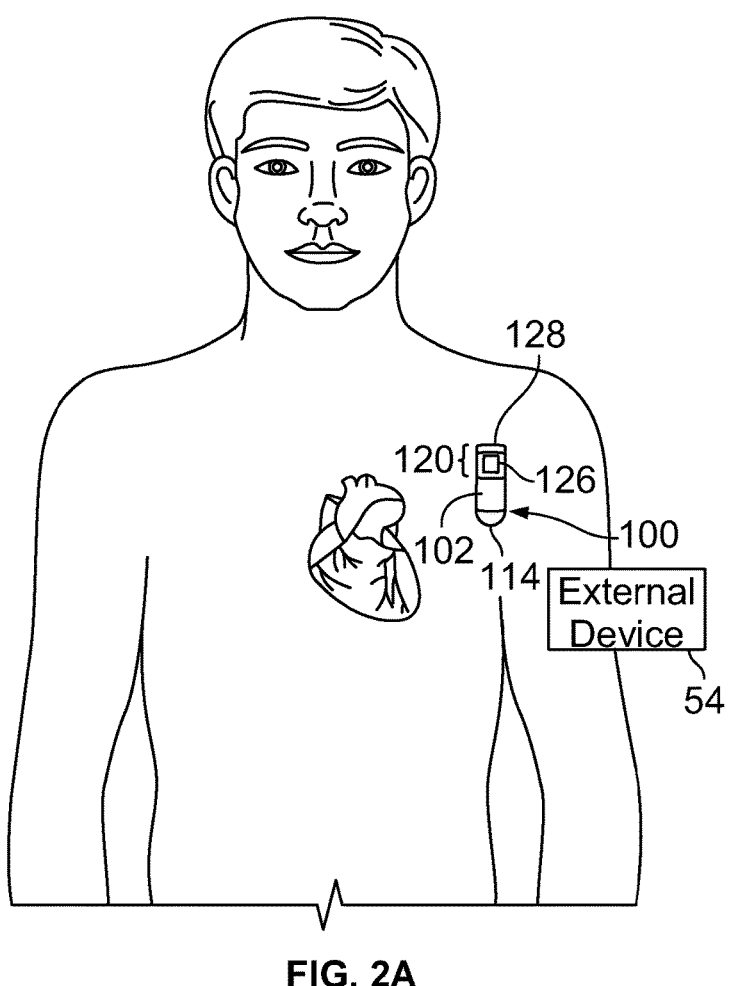
FIG. 2A illustrates a leadless IMD intended for subcutaneous implantation at a site near the heart in accordance with another embodiment.

FIG. 2A illustrates a leadless IMD 100 intended for subcutaneous implantation at a site near the heart. In a non-limiting example, the IMD 100 is an implantable cardiac monitoring (ICM) device. The IMD 100 optionally performs cardiac rhythm management (CRM) applications. Unlike the IMD 8 in FIG. 1, the IMD 100 does not include any leads. The IMD 100 includes a case 102, or device housing, that is mechanically joined to a header 120. The header 120 holds at least one sensing electrode 126 and an antenna 128 within an interior of the header 120. The case 102 may be programmable to act as an electrode for certain sensing modes. The header 120 does not have any ports for connecting to leads.

The case 102 includes one or more electrodes 114 that are provided on the case 102 distal from the header 120. The electrode(s) 114 may be located at various locations on the case 102. For example, when separate housing portions are provided for the electronics module and the battery, one or more electrodes may be located on the battery (e.g., the battery housing). Numerous configurations of electrode arrangements are possible.

The case 102 holds electronic components for computing, data storage, and/or processing functions of the IMD 100.

The case 102 may contain sensing electronics for receiving signals from the electrodes, a microprocessor for processing the signals in accordance with algorithms (e.g., an atrial fibrillation (AF) detection algorithm), a memory for temporary storage of electrograms, a device memory for long-term storage of electrograms upon certain triggering events (e.g., AF detection), sensors for detecting patient activity, and a battery for powering components.

The IMD 100 may sense far field, subcutaneous electrograms, process the electrograms to detect arrhythmias, and automatically record the electrograms in the memory for subsequent transmission through the antenna 128 to an external device 54. Electrogram processing and arrhythmia detection is provided for, at least in part, by algorithms embodied in the microprocessor. The external device 54 may be similar to the external device 16 in FIG. 1.

Figure 2B:
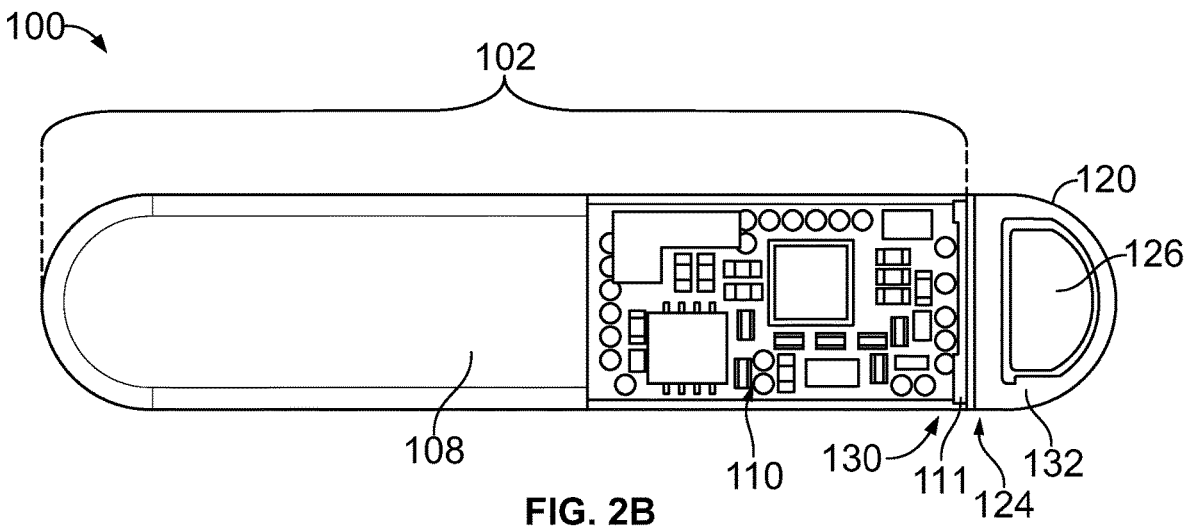
FIG. 2B illustrates a plan view of the leadless IMD shown in FIG. 2A.

FIG. 2B illustrates a plan view of the leadless IMD 100 shown in FIG. 2A. The header 120 is mounted to the case 102 via a feedthrough assembly 111 of the IMD 100. The feedthrough assembly 111 is disposed between the header 120 and the case 102, and mechanically couples the header 120 to the case 102. The header 120 has a mounting end 124 configured to be mounted to the feedthrough assembly 111. The case 102 has a mounting end 130 that affixes to the opposite side or end of the feedthrough assembly 111 as the header 120.

Figure 3:
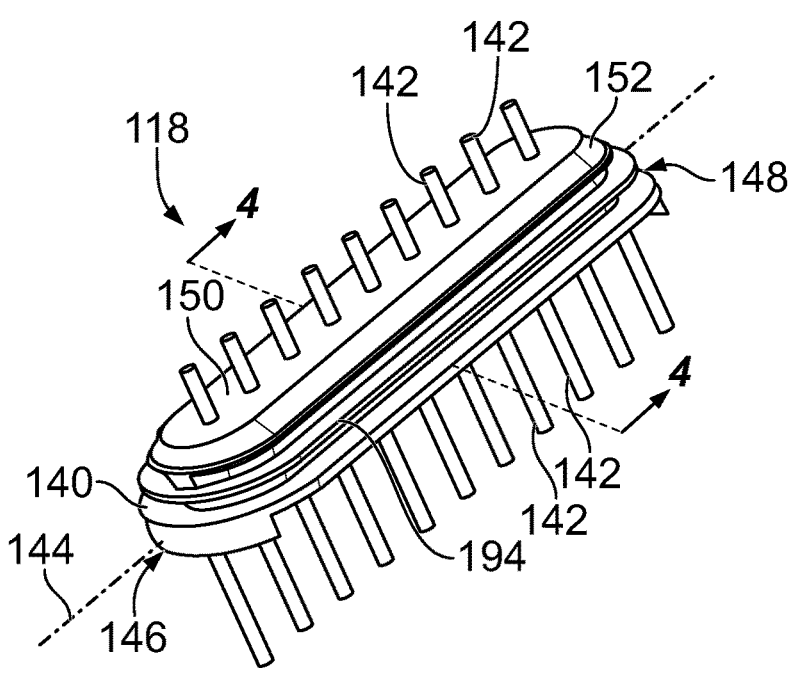
FIG. 3 is a perspective view of a feedthrough assembly of an IMD according to an embodiment.

The sensing electrode 126 and the antenna 128 of the header 120 are electrically connected to the electronics module 110 via electrically conductive elements of the feedthrough assembly 111 (e.g., the conductive elements 142 shown in FIG. 3). In the illustrated embodiment, the antenna 128 is not visible because it is disposed within an interior volume of a header body 132 of the header 120. The header body 132 represents a solid (non-hollow) body formed of a generally homogeneous dielectric (e.g., electrically insulative) material.

The assembly process of the IMD 100 may include electrically connecting the battery 108 to the electronics module 110 to power the electronics module 110. The battery 108 and the electronics module 110 may be loaded into one of the housing case portions or shells. The conductive elements of the feedthrough assembly 111 may then be electrically connected to the electronics module 110. The header 120 is mounted to the feedthrough assembly 111 in a way that includes electrically connecting the sensing electrode 126 and the antenna 128 to the conductive elements of the feedthrough assembly 111. The two case portions of the case 102 may be coupled together to enclose the battery 108 and the electronics module 110. Optionally, the assembly steps may be performed in a different order than described above. Once the IMD device 100 is coupled together, the interfaces between the case portions of the case 102 and the interface between the header 120 and the case 102 at the feedthrough assembly 111 are sealed. For example, at least one of the interfaces may be welded, filled with a sealant, bonded using a braze material or an adhesive, or the like, to hermetically seal the interior components of the IMD 100 from the organic tissues and fluids of the patient that form the external environment.

FIG. 3 is a perspective view of a feedthrough assembly 118 of an IMD according to an embodiment. The feedthrough assembly 118 according to embodiments described herein may be used with IMDs that include one or more leads (e.g., the IMD 8 in FIG. 1) as well as with leadless IMDs (e.g., the IMD 100 in FIGS. 2A and 2B). For example, the feedthrough assembly 118 may be the feedthrough assembly 111 of the IMD 100 shown in FIGS. 2A and 2B.

Optionally, the feedthrough assembly 118 may be a component of the IMD 8 in FIG. 1. For example, the feedthrough assembly 118 may be mounted to the case 10 at the location where the leads 11 project from the case 10 towards the heart 9. The feedthrough assembly 118 is designed to provide and maintain hermeticity of the device housing (e.g., the case 10 in FIG. 1 and/or the case 102 in FIGS. 2A and 2B) when installed within the electrolytic environment of the patient body. Although the feedthrough assembly 118 is occasionally referred to herein with reference to components of the leadless IMD 100 of FIGS. 2A and 2B, it is understood that the feedthrough assembly 118 may be installed in other types of IMDs in other embodiments.

The feedthrough assembly 118 includes a housing 140 and one or more electrically conductive elements 142 that extend through a height of the housing 140. In the illustrated embodiment, the housing 140 is elongated along a longitudinal axis 144 of the assembly 118 from a first end 146 of the housing 140 to a second end 148 of the housing 140 opposite the first end 146. The ends 146, 148 of the housing 140 are curved, such that the housing 140 generally has an oval or elliptical shape. The housing 140 may have other shapes in other embodiments, such as a rectangular shape, a circular shape, or the like.

The electrically conductive elements 142 provide electrical signals and/or power between the header 120 and the case 102, as shown in FIGS. 2A and 2B. The conductive elements 142 are insulated wires in the illustrated embodiment. Optionally, one or more of the conductive elements 142 may be pins, receptacle connectors, plug connectors, uninsulated wires, and/or the like, instead of insulated wires. In the illustrated embodiment, the conductive elements 142 are linearly arranged in a line parallel to the longitudinal axis 144. In an alternative embodiment, the feedthrough assembly 118 may include a different number and/or arrangement of the conductive elements 142 than shown in FIG. 3. Optionally, the feedthrough assembly 118 may include as few as one conductive element 142.

The electrically conductive elements 142 may be wires, pins, receptacle connectors, plug connectors, and/or the like. The electrically conductive elements 142 project through a height of the feedthrough assembly. The electrically conductive elements 142 project through the mounting end 124 of the header 120 to electrically connect to the antenna 128 and the sensing electrode 126. For example, a first conductive element 142 may electrically connect, via welding, connectors, or the like, to the antenna 128, and a second conductive element 142 may electrically connect to the sensing electrode 126. The electrically conductive elements 142 also project through the mounting end 130 of the case 102 to electrically connect to the battery 108 and the electronics module 110. In an embodiment, the conductive elements 142 directly connect to the electronics module 110, via welding, connectors, or the like, and indirectly connect to the battery 108 via the intervening electronics module 110.

The feedthrough assembly 118 also includes a non-corrosive sealant 150 that is applied on the feedthrough assembly 118 to inhibit corrosion and maintain hermeticity of the IMD 100. For example, the presence of the non-corrosive sealant 150 may insulate corrosion-susceptible surfaces, reducing the likelihood of such surfaces being exposed to corrosive substances. The non-corrosive sealant 150 in the illustrated embodiment forms a cover layer 152 that coats a majority of a top side 160 (shown in FIG. 4) of the housing 140. The non-corrosive sealant 150 individually surrounds each of the conductive elements 142 along a segment of the respective conductive element 142 that protrudes beyond the top side 160 of the housing 140. For example, portions of the non-corrosive sealant 150 extend into the spaces between adjacent conductive elements 142, and the non-corrosive sealant 150 contacts and conforms around the entire perimeter surface of each conductive element 142.

Figure 4:
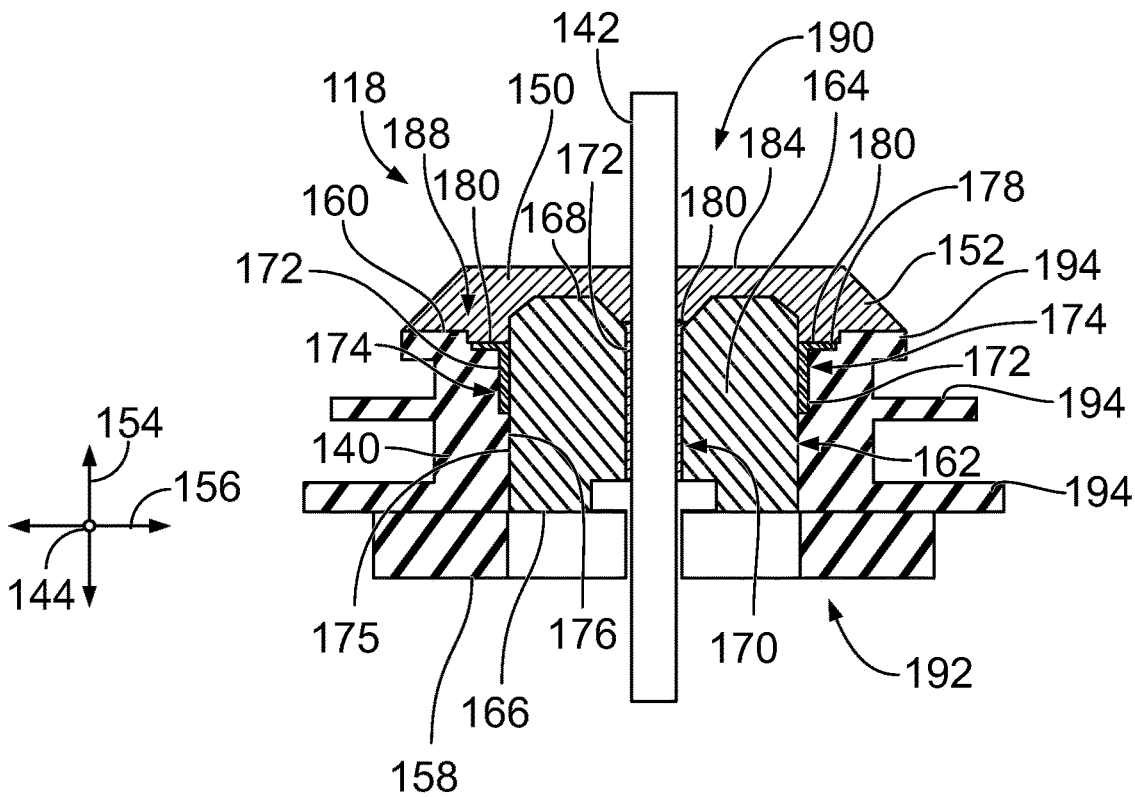
FIG. 4 is a cross-sectional view of the feedthrough assembly shown in FIG. 3 taken along line 4-4 in FIG. 3.

FIG. 4 is a cross-sectional view of the feedthrough assembly 118 shown in FIG. 3 taken along line 4-4 in FIG. 3. The view in FIG. 4 extends along the longitudinal axis 144. The housing 140 has a height along a vertical axis 154 of the feedthrough assembly 118 and a width along a lateral axis 156 of the feedthrough assembly 118. The axes 144, 154, 156 are mutually perpendicular. The height of the housing 140 extends from a bottom side 158 to a top side 160. When assembled in the IMD 100, the bottom side 158 faces the case 102, and the top side 160 faces the header 120. Directional terms used herein, such as top, bottom, left, right, upper, and lower, are based on the illustrated orientations shown in the figures and are used to support the description of the figures, not to impose orientational limitations on the IMD 100 and/or the feedthrough assembly 118 relative to the surrounding environment.

The feedthrough assembly 118 has a header side 190 that mounts to the header 120 and a case side 192 that mounts to the case 102. The header side 190 is the top of the feedthrough assembly 118 in the illustrated embodiment, and the case side 192 is the bottom of the feedthrough assembly 118. The header side 190 is defined by the non-corrosive sealant 150 in FIG. 4, and the case side 192 is defined by the bottom surface 158 of the housing 140. Each of the electrically conductive elements 142 projects from the feedthrough assembly 118 beyond the header side 190 into the header 120, and beyond the case side 192 into the case 102. For example, a respective first segment of each conductive element 142 is disposed along the height of the feedthrough assembly 118 (e.g., is surrounded by and contacted by the feedthrough assembly 118), a second segment of each conductive element 142 projects beyond the header side 190 and extends into the header 120 to electrically connect to the antenna 128, the electrode 126, or the like, and a third segment of each conductive element 142 projects beyond the case side 192 and extends into the case 102 to electrically connect to the electronics module 110.

The housing 140 defines a central cavity 162 that extends through the height of the housing 140 from the top side 160 to the bottom side 158. The central cavity 162 is elongated along the longitudinal axis 144 shown in FIG. 3. The housing 140 includes protrusions 194 along an outer perimeter of the housing 140 for coupling to the header 120 and/or the case 102. The protrusions 194 may be ridges, shelves, tabs, or the like. The protrusions 194 may be elongated along the length of the housing 140, as shown in FIG. 3. The protrusions 194 may support coupling the feedthrough assembly 118 to the header 120 by providing a friction fit, enabling a flowable overmold material of the header body 132 (FIG. 2B) to conform around the protrusions 194, or the like. In a non-limiting example, the feedthrough assembly 118 may be placed into a mold and a flowable overmold material is then supplied into the mold to form the header body 132 in-situ on the header side 190 of the feedthrough assembly 118. The overmold material, which forms the header body 132, may be an insulative (e.g., dielectric) material that covers at least part of the non-corrosive sealant 150.

The feedthrough assembly 118 includes a solid insert 164 disposed within the central cavity 162 of the housing 140. The solid insert 164 is not visible in FIG. 3 because it is concealed by the housing 140 and the non-corrosive sealant 150. The solid insert 164 is elongated along the longitudinal axis 144, similar to the housing 140. The solid insert 164 extends a height from a bottom surface 166 of the insert 164 to a top surface 168 of the insert 164 opposite the bottom surface 166. The solid insert 164 defines multiple apertures 170 that extend through the height of the solid insert 164 (from the bottom surface 166 to the top surface 168). The apertures 170 are spaced apart from each other. The apertures 170 are sized such that each aperture 170 accommodates one corresponding conductive element 142. FIG. 4 shows one aperture 170 and one conductive element 142 that extends through the depicted aperture 170. In the illustrated embodiment shown in FIGS. 3 and 4, the conductive elements 142 are arranged in a line, with each element 142 extending through a different corresponding aperture 170 of the solid insert 164. The insert 164 is disposed within the central cavity 162 of the housing 140, so all of the conductive elements 142 extend through the central cavity 162.

The feedthrough assembly 118 includes a metal filler 172 at component interfaces. For example, the metal filler 172 joins together the solid insert 164 and the housing 140. The metal filler 172 may bond the solid insert 164 to the housing 140, which fixedly secures the solid insert 164 within the central cavity 162 of the housing 140. At least some of the metal filler 172 is disposed within a joint 174 defined between an outer surface 175 of the solid insert 164 and an inner surface 176 of the housing 140. The outer surface 175 of the solid insert 164 is an outer perimeter surface of the solid insert 164. The inner surface 176 of the housing 140 is a surface that defines the dimensions of the central cavity 162. The joint 174 may be a closed loop that is elongated along the longitudinal axis 144. The metal filler 172 may be deposited into the joint 174 along the entire length of the joint 174 such that the metal filler 172 seals the joint 174. In the illustrated embodiment, a portion of the metal filler 172 may coat a top surface 178 of the housing 140 above the joint 174.

The metal filler 172 is also disposed in the aperture 170 between the conductive element 142 and the solid insert 164. The metal filler 172 may fill the open space between the conductive element 142 and the inner surface of the solid insert 164 that defines the aperture 170 to seal the aperture 170. The metal filler 172 may bond the conductive element 142 to the solid insert 164, which fixedly secures the conductive element 142 within the aperture 170. Although only one aperture 170 is shown in FIG. 4, the metal filler 172 may be disposed in a plurality of the apertures 170, such as every aperture 170. The metal filler 172 essentially seals the joint, or open space, between the conductive elements 142 and the inner surfaces of the solid insert 164 defining the apertures 170.

In the illustrated embodiment, the non-corrosive sealant 150 coats a top surface 180 of the metal filler 172 to inhibit corrosion of the metal filler 172. The non-corrosive sealant 150 may also coat additional components besides the metal filler 172, such as adjacent portions of the housing 140 and/or the conductive elements 142, and any intermetallic compounds present. The intermetallic compounds may be formed during processing, such as via two metals fusing or chemically reacting. The intermetallic compounds may be located within the joint 174 and/or proximate to the joint 174. The non-corrosive sealant 150 may be directly coated on the top surface 180 of the metal filler 172 at least a portion of the adjacent housing 140, and/or at least a portion of the conductive elements 142. The sealant 150 may protect the metal filler 140 and any other corrosion-susceptible material underneath the sealant 150 (e.g., intermetallic compounds, conductive elements, and/or housing) from exposure to an electrolytic body fluid when implanted within a patient. The sealant 150 is designed to prevent, or at least inhibit, corrosion of the underlying materials, although it is possible for a small and/or de minim is amount of corrosion to occur in some instances even with the sealant 150 present. The non-corrosive sealant 150 covers both the metal filler 172 located in the joint 174 and the metal filler 172 located in each of the apertures 170. In the illustrated embodiment, the non-corrosive sealant 150 also directly coats at least a majority of the top surface 168 of the solid insert 164 and a majority of the top side 160 (e.g., top surface 178) of the housing 140.

Figure 5:
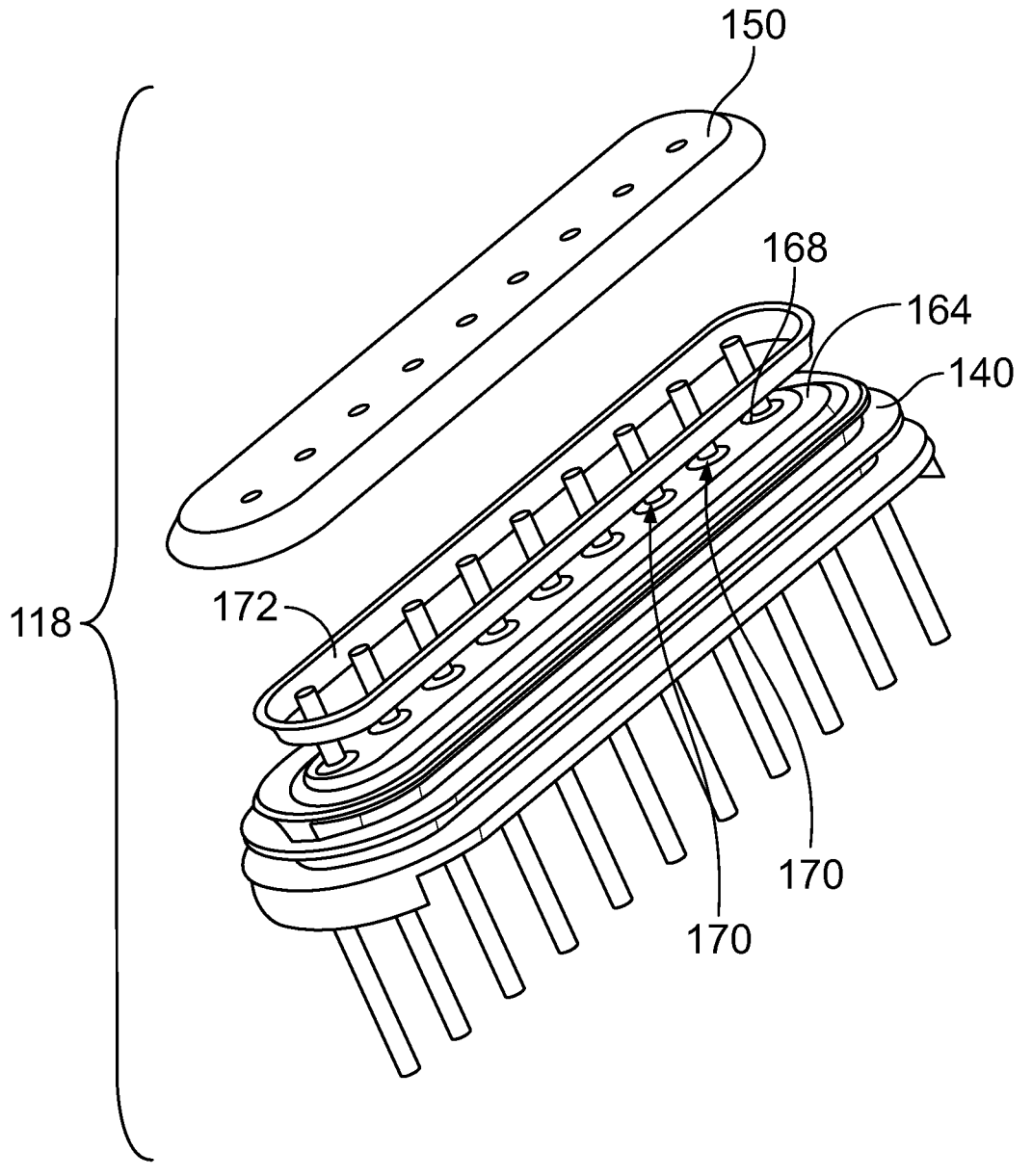
FIG. 5 is an exploded perspective view of the feedthrough assembly shown in FIGS. 3 and 4.

FIG. 5 is an exploded perspective view of the feedthrough assembly 118 shown in FIGS. 3 and 4. FIG. 5 shows the elongated top surface 168 of the solid insert 164, and the apertures 170 arranged in a row. The metal filler 172 is shown as a closed-loop ribbon, and the non-corrosive sealant 150 is shown as a planar cover layer. In at least one embodiment, the metal filler 172 is formed in-situ by depositing the filler material in a flowable state onto the solid insert 164 and the housing 140. The flowable material conforms to the shapes of the solid objects and then subsequently solidifies. The non-corrosive sealant 150 may be formed in-situ, in addition to the metal filler 172, by depositing the sealant 150 in a flowable state onto the solid insert 164 and/or the solid metal filler 172 to conform to the shapes of the solid and then solidify. Thus, it is recognized that FIG. 5 is an exploded view of the completed feedthrough assembly 118, when the non-corrosive sealant 150 and the metal filler 172 are in the solid, formed state, rather than a view showing an intermediate stage of the assembly process.

Returning now to FIG. 4, the metal filler 172 in an embodiment is a braze material that is deposited into the joint 174 during a brazing process. The metal filler 172 may be a pure metal, such as gold. Alternatively, the metal filler 172 may be a braze alloy that includes one or more of aluminum, silicon, copper, zinc, tin, silver, gold, nickel, or the like. The specific composition of the metal filler 172 may be based on the compositions of the solid insert 164 and the housing 140, to ensure that the metal filler 172 is able to adhere or "wet" to both the insert 164 and the housing 140.

Optionally, the housing 140 has a stepped top surface 178, such that an area of the top surface 178 is within a groove or depression 188 relative to the remainder of the top surface 178. The joint 174 extends downward from the groove 188. The groove 188 represents a trough that holds the excess portion of the metal filler 172 that emerges from the top of the joint 174. That excess portion defines the top surface 180 of the metal filler 172 which is coated by the non-corrosive sealant 150. In an alternative embodiment, the entire top surface 178 of the housing 140 may be planar (e.g., along the same plane).

In at least one embodiment, the housing 140 includes a metal material, and the solid insert 164 includes a ceramic material. The metal filler 172 is selected to adhere to both the metal material of the housing 140 and the ceramic material of the insert 164. In a non-limiting example, the housing 140 is composed of titanium, and the solid insert 164 is composed of alumina. The metal filler 172 may be or include gold, which can adhere to both titanium and alumina during a brazing process. When the solid insert 164 is composed of a ceramic material, the insert 164 may be electrically insulative (e.g., a dielectric). In another embodiment, the solid insert 164 may be composed of a metal material that is electrically conductive.

Optionally, the non-corrosive sealant 150 is applied to cover and coat all material between the housing 140 and solid insert 164, which includes the metal filler 172 and any accompanying intermetallic compounds that may have formed during processing, for protecting the coated material from corrosive environments. For example, if the top surface 180 of the metal filler 172 is left uncovered (e.g., if the feedthrough assembly 118 is formed without the non-corrosive sealant 150), it is possible that the metal filler 172, intermetallic compounds, and the like, may eventually be exposed to an electrolytic solution, such as body fluid of the patient into which the IMD is implanted. In the illustrated embodiment of the IMD 100 shown in FIGS. 1 and 2, the header 120 encases the top end of the feedthrough assembly 118, which is designed to protect the metal filler 172 from the electrolytic body fluid. However, if a leak path forms through the header 120 or at the interface between the header 120 and the feedthrough assembly 118, the body fluid may penetrate the header 120 and reach the top surface 180 of the metal filler 172 (and any other corrosion-susceptible materials, including intermetallic compounds). Furthermore, in different and/or future embodiments, particularly embodiments the attempt to reduce form factor size, the IMD 100 may lack a discrete header. As such, the metal filler 172 may be exposed to the external environment along an exterior of the feedthrough assembly 118. Upon prolonged exposure to body fluid or another electrolytic solution, the metal filler 172 and any other corrosion-susceptible materials may degrade and corrode. Eventually, the corroded metal filler 172 and/or other corrosion-susceptible materials may form a leak path that enables the fluid to flow through the joint 174 and enter the internal cavity of the case 102. The electrolytic solution and/or humidity may damage the electronic module 110, the battery 108, and/or the associated circuitry within the case 102, which can cause premature aging and/or complete non-functionality of the IMD 100.

By coating any exposed surfaces of the metal filler 172 and accompanying intermetallic compounds with the non-corrosive sealant 150, the feedthrough assembly 118 according to the embodiments described herein demonstrates enhanced resistance to corrosion and other chemical and electrochemical reactions, relative to feedthrough assemblies that do not coat metal surfaces with non-corrosive sealants, when in harsh environments. The non-corrosive sealant 150 is biocompatible, biostable, and has long-term reliability, such that the sealant 150 does not harm the patient if exposed to body fluid.

In an embodiment, the non-corrosive sealant 150 is electrically insulative. For example, the sealant 150 may be composed of alumina, parylene, polyurethane, silicone, and/or an epoxy material. The specific composition of the sealant 150 may be selected based on various factors, such as the application technique used to deposit the sealant 150 on the feedthrough assembly 118. The sealant 150 covers at least a majority of the top surface 168 of the solid insert 164. The sealant 150 also covers a majority of the top surface 178 of the housing 140. In the illustrated embodiment, the sealant 150 covers the entirety of the top surface 168 of the solid insert 164 and most of the top surface 178 of the housing 140. The sealant 150 optionally may fully cover the entire top surface 178 of the housing 140. The sealant 150 is applied to form the cover layer 152. The sealant 150 has a noticeable thickness, and a top surface 184 of the sealant 150 defines the top or header side 190 of the feedthrough assembly 118. The sealant 150 contacts and fully surrounds a segment of the conductive elements 142 that aligns with the cover layer 152. Such segments of the conductive elements 142 protrude beyond the top surface 168 of the solid insert 164.

The cover layer 152 may be formed by applying the sealant 150 on the top of the solid insert 164, the metal filler 172, and the housing 140 after the feedthrough assembly 118 is assembled. The sealant 150 may be deposited in a flowable state to enable the sealant 150 to fill voids and conform to solid structures. In a non-limiting example, the sealant 150 may be applied via casting or molding, a deposition technique, or the like.

The casting technique may include solvent casting or dispensing. Solvent casting involves dissolving the non-corrosive sealant 150 material into a solvent, dispensing the resulting mixture on the feedthrough assembly 118, and then allowing the solvent in the mixture to evaporate. The dispensing may include dispensing or casting the non-corrosive sealant 150 to cover the desired area of the feedthrough assembly 118. The dispensing may be performed using a precision fluid dispensing instrument.

The molding technique may include injection molding the non-corrosive sealant 150 material into a mold when in a flowable state to solidify into the shape of the mold. The injection molding may be a pre-mold, in which the non-corrosive sealant 150 is formed and then removed from the mold and subsequently attached or bonded to the desired area on the feedthrough assembly 118. Alternatively, the injection molding may be performed in-situ on the feedthrough assembly 118 by directly injecting the sealant material onto the desired area of the feedthrough assembly 118.

The deposition technique may be physical vapor deposition, chemical vapor deposition, or the like. Physical vapor deposition involves sputtering material onto the desired area of the feedthrough assembly 118. The sputtering may be reactive sputtering that uses gases for oxides or nitrites. Alternatively, the sputtering may be non-reactive to sputter pure metals such as titanium, niobium, tantalum, platinum, or the like, which would represent the non-corrosive sealant 150. The chemical vapor deposition can involve depositing a conformal material such as silicone, parylene, polyurethan, or the like, as the non-corrosive sealant 150.

Figure 6:
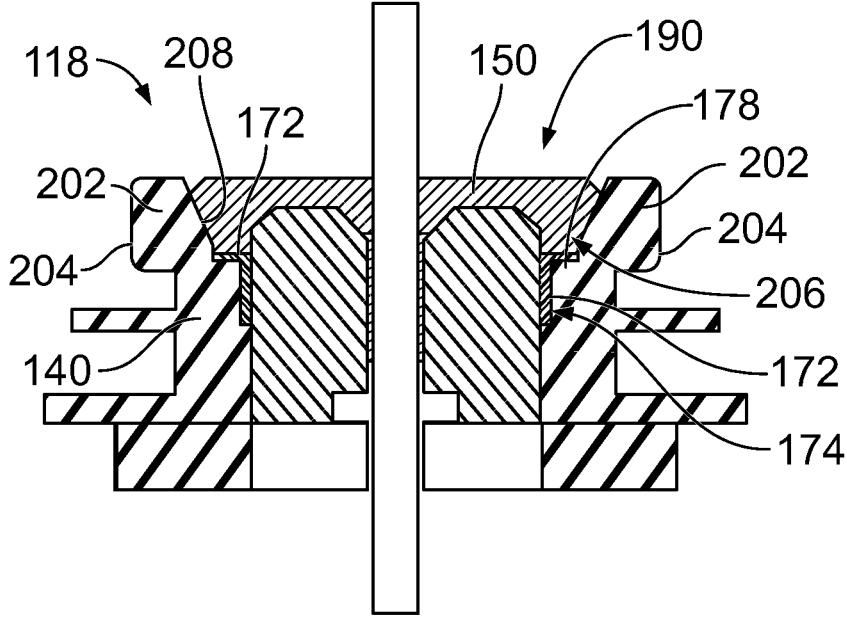
FIG. 6 is a cross-sectional view of the feedthrough assembly according to another embodiment.
Figure 7:
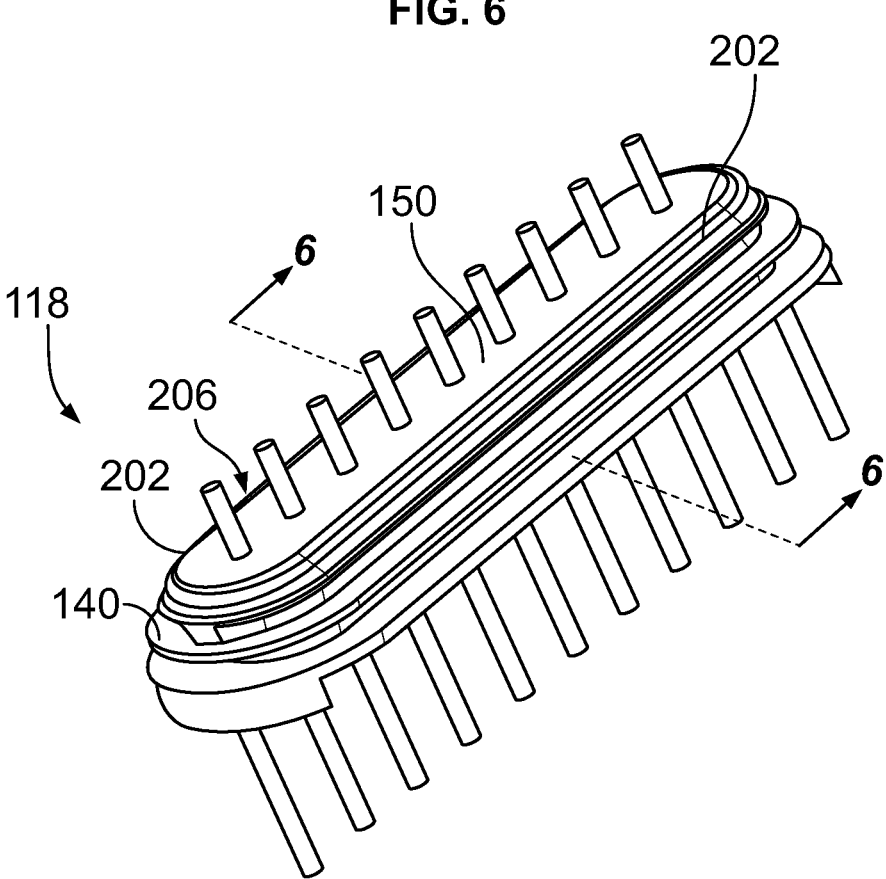
FIG. 7 is a perspective view of the feedthrough assembly shown in FIG. 6.

FIG. 6 is a cross-sectional view of the feedthrough assembly 118 according to another embodiment. FIG. 7 is a perspective view of the feedthrough assembly 118 shown in FIG. 6. The cross-section in FIG. 6 is taken along line 6-6 in FIG. 7. The illustrated embodiment is similar to the embodiment shown in FIGS. 3 through 5 except for a modification to the housing 140. The housing 140 in the illustrated embodiment has a raised lip 202 that projects from the top surface 178 of the housing 140. The raised lip 202 is disposed at an outer edge 204 of the top surface 178, and continuously extends along the outer perimeter of the housing 140, as shown in FIG. 7. The raised lip 202 defines an outer barrier of a well 206 that encompasses the joint 174 and the metal filler 172.

The non-corrosive sealant 150 is deposited within the well 206, and at least partially fills the well 206. For example, the non-corrosive sealant 150 may be injected, poured, deposited, or dispensed into the well 206 when in a flowable state (e.g., liquid or semi-liquid). The raised lip 202 forces the flowable sealant 150 to pool within the well 206, covering the metal filler 172. Forming the well 206 along the header side 190 of the feedthrough assembly 118 may ease the sealant 150 application process by providing a barrier to confine the flowable material. The raised lip 202 optionally may have an angled inner surface 208 that funnels the flowable sealant material towards the metal filler 172.

Figure 8:
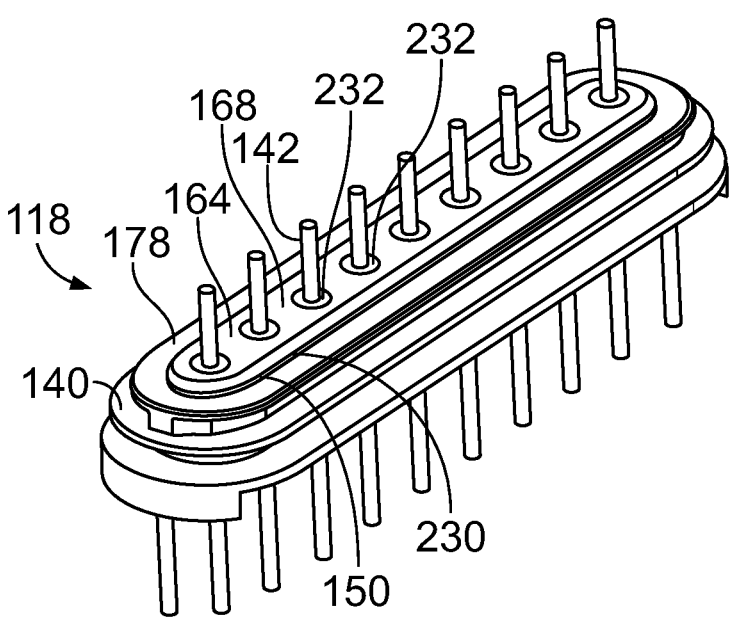
FIG. 8 is a perspective view of the feedthrough assembly according to another embodiment.

FIG. 8 is a perspective view of the feedthrough assembly 118 according to another embodiment. In the illustrated embodiment, the non-corrosive sealant 150 is applied as individual beads instead of the cover layer 152 shown in the embodiments depicted in FIGS. 3 through 7.

In the illustrated embodiment, the non-corrosive sealant 150 is in the form of an elongated bead 230 which extends along the length of the joint 174 without covering much, if any, of the top surface 168 of the solid insert 164 or the top surface 178 of the housing 140. The elongated bead 230 is generally oval in shape. The bead 230 is applied directly on the metal filler (not shown) at the interface between the solid insert 164 and the housing 140 to coat the top surface of the metal filler and protect the metal filler and accompanying intermetallic compounds from electrolytic solutions. The bead 230 may cover a small portion of the solid insert 164 and/or the housing 140, but does not cover a majority of the respective top surface 168, 178 of either component. The non-corrosive sealant 150 is also in the form of multiple annular beads 232 that surround the individual conductive elements 142. For example, each annular bead 232 may have a circular, ring-shape that surrounds a corresponding one of the conductive elements 142, covering the metal filler within the aperture 170 (shown in FIG. 4) of the solid insert 164. Each annular bead 232 may cover little, if any, of the top surface 168 of the solid insert 164 (and none of the top surface 178 of the housing 140).

Figure 9:
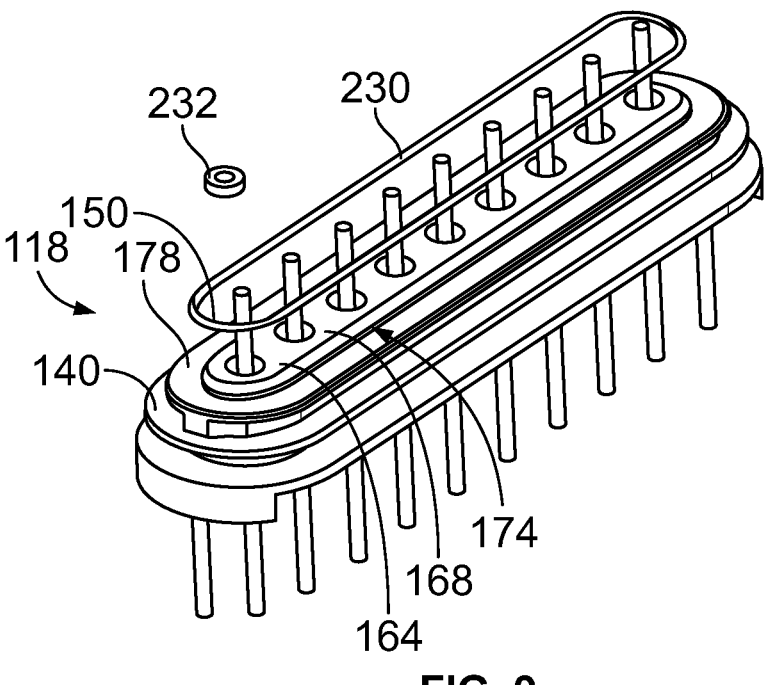
FIG. 9 is a partially-exploded perspective view of the feedthrough assembly shown in FIG. 8.

FIG. 9 is a partially-exploded perspective view of the feedthrough assembly 118 shown in FIG. 8 showing the elongated bead 230 and one of the annular beads 232 suspended above the housing 140 and the solid insert 164. Applying the non-corrosive sealant 150 as the beads 230, 232 instead of the cover layer 152 may efficiently conserve sealant material.

The non-corrosive sealant 150 that forms the beads 230, 232 may be composed of one or more of the materials described above with respect to FIG. 4. In a non-limiting example, the non-corrosive sealant 150 may be electrically conductive. For example, the non-corrosive sealant 150 may be composed of a metal material that has non-corrosive properties, such as titanium, niobium, tantalum, platinum, or the like. The metal material may be deposited into the beads 230, 232 via brazing, precision fluid dispensing, physical or chemical vapor deposition, or the like. In an alternative example, the non-corrosive sealant 150 may be electrically insulative, such as composed of alumina, parylene, polyure-thane, silicone, or an epoxy material.

Figure 10:
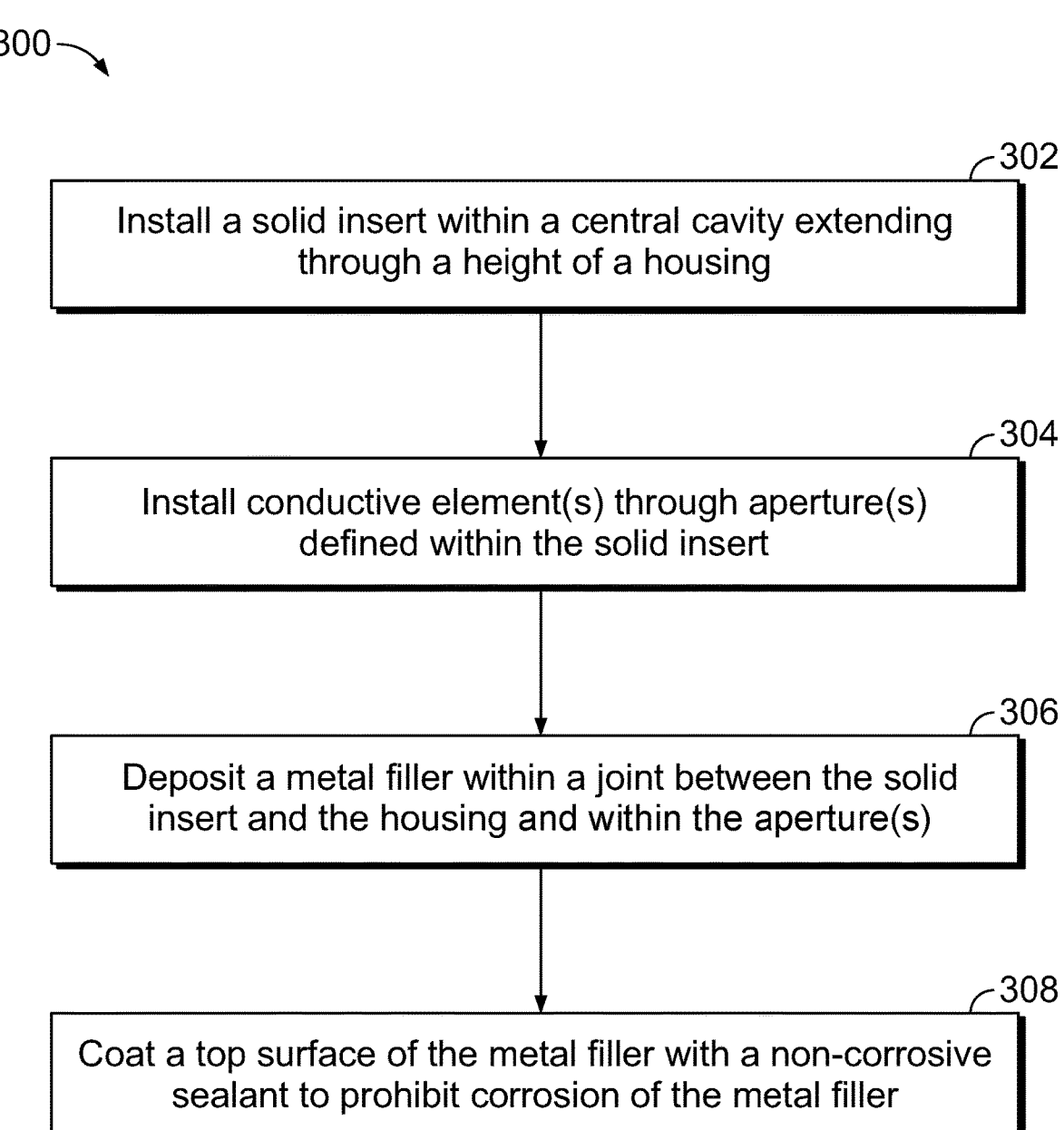
FIG. 10 is a flow chart of a method for producing a feedthrough assembly according to an embodiment.

FIG. 10 is a flow chart 300 of a method for producing a feedthrough assembly according to an embodiment. The method may include additional steps than shown in FIG. 10, fewer steps than shown in FIG. 10, and/or different steps than shown in FIG. 10. Furthermore, the order of the steps presented in FIG. 10 is not a limitation unless one step is specifically described as following or based on another step.

Referring to FIGS. 1 through 9, the method begins at 302, at which a solid insert 164 is installed within a central cavity 162 of a housing 140. The central cavity 162 extends through a height of the housing 140. At 304, one or more electrically conductive elements 142 are installed through one or more apertures 170 defined within the solid insert 164. At 306, a metal filler 172 is deposited within a joint 174 and/or within the apertures 170. The joint 174 is defined by an outer surface 175 of the solid insert 164 and an inner surface 176 of the housing 140. The inner surface 176 defines the perimeter of the central cavity 162.

At 308, a top surface 180 of the metal filler 172 is coated with a non-corrosive sealant 150 to prohibit, or at least inhibit, corrosion of the metal filler 172. Optionally, the non-corrosive sealant 150 may be coated on the top surface 180 of the metal filler 172 via one of chemical vapor deposition, physical vapor deposition, injection molding, precision fluid dispensing, or casting. In non-limiting examples, the non-corrosive sealant 150 is composed of alumina, parylene, polyurethane, silicone, or an epoxy mate-rial, the solid insert 164 is composed of a ceramic material, and the housing 140 is composed of a metal material.

In an embodiment, the non-corrosive sealant 150 is coated on the top surface 180 of the metal filler 172 to also coat at least a majority of a top surface 168 of the solid insert 164. The non-corrosive sealant 150 forms a cover layer 152 that individually surrounds each of the one or more conductive elements 142 along a segment of the respective conductive element 142 that protrudes beyond the top surface 168 of the solid insert 164. Optionally, the housing 140 has a raised lip 202 that projects from a top surface 178 of the housing 140 and extends along an outer perimeter of the housing 140. The raised lip 202 defines an outer edge 204 of a well 206 that encompasses the joint 174 and the metal filler 172. The non-corrosive sealant 150 is coated on the top surface 180 of the metal filler 172 by at least partially filling the well 206 with the non-corrosive sealant 150.

In another embodiment, the non-corrosive sealant 150 is coated on the top surface 180 of the metal filler 172 by applying a bead 230 of the non-corrosive sealant 150 along a full length of the joint 174 without coating or covering a majority of a top surface 168 of the solid insert 164 or a majority of a top surface 178 of the housing 140 with the non-corrosive sealant 150.

Figure 11:
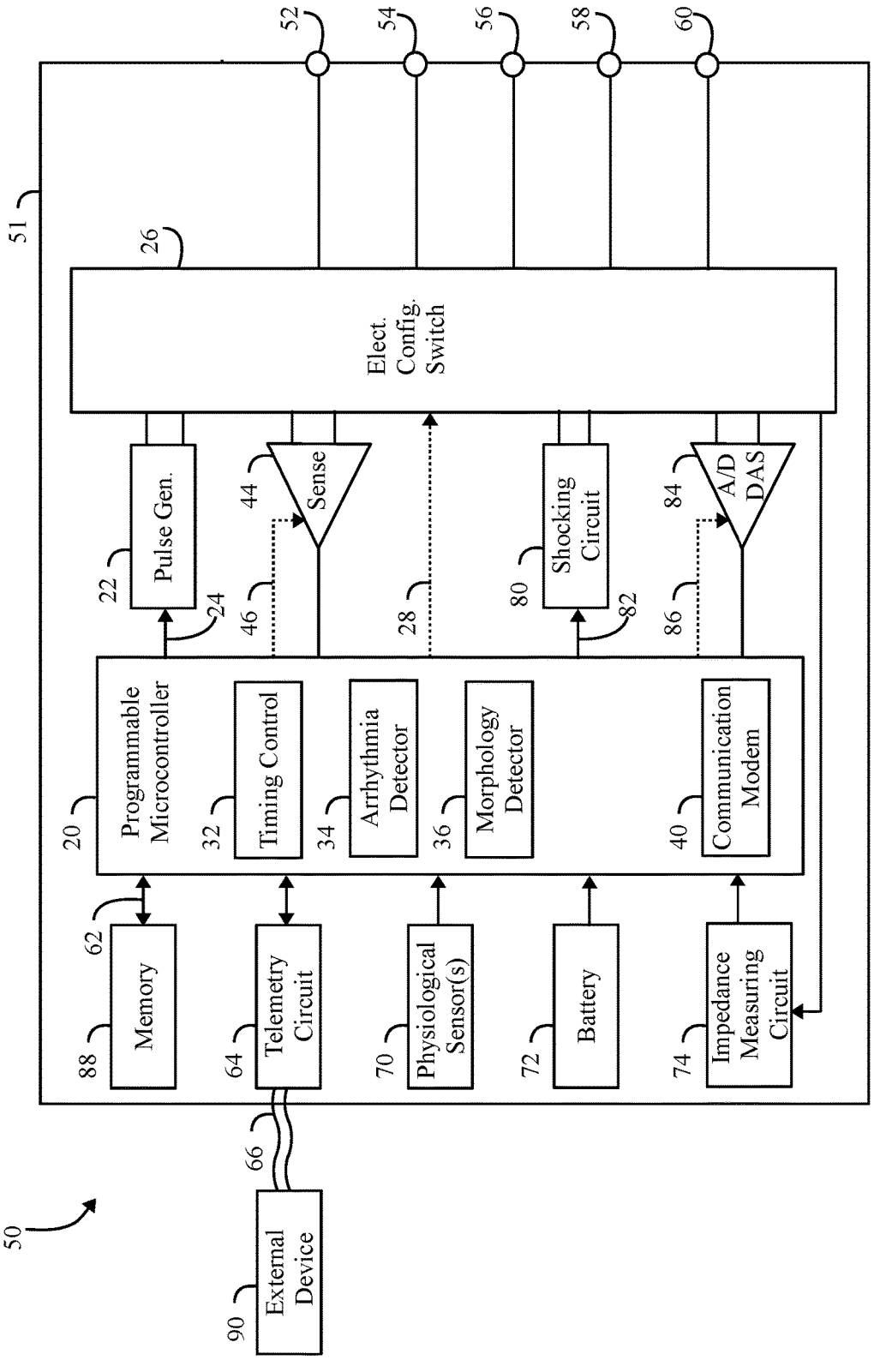
FIG. 11 shows a block diagram of an exemplary IMD that is configured to be implanted into the patient in accordance with embodiments herein.

FIG. 11 shows a block diagram of an IMD 50 that is configured to be implanted into a patient. The IMD 50 may represent the IMD 8 shown in FIG. 1. The IMD 50 may be implemented to monitor ventricular activity alone, or both ventricular and atrial activity through sensing circuit. The IMD 50 may treat both fast and slow arrhythmias with stimulation therapy, including cardioversion, pacing stimu-lation, an implantable cardioverter defibrillator, suspend tachycardia detection, tachyarrhythmia therapy, and/or the like. Several components in the IMD 50 may be the same or similar to components of the IMD 100 shown in FIGS. 2A and 2B.

The IMD 50 has a device case (or housing) 51 to hold the electronic/computing components. The case 51 (which can also be referred to as the "housing," "can," "encasing," or "case electrode") may be programmably selected to function as an electrode for certain sensing modes. Case 51 further includes a connector (not shown) with at least one terminal 52 and optionally additional terminals 54, 56, 58, 60. The terminals may be connected to electrodes that are located in various locations within and about the heart. The type and location of each electrode may vary. For example, the electrodes may include various combinations of ring, tip, coil, shocking electrodes, and the like.

The IMD 50 includes a programmable microcontroller 20 that controls various operations of the IMD 50, including cardiac monitoring and stimulation therapy. Microcontroller 20 includes a microprocessor (or equivalent control cir-cuitry), RAM and/or ROM memory, logic and timing cir-cuitry, state machine circuitry, and I/O circuitry. Microcon-troller 20 includes an arrhythmia detector 34 that is configured to cardiac activity data to identify potential AF episodes as well as other arrhythmias (e.g., Tachycardias, Bradycardias, Asystole, etc.).

An electrode configuration switch 26 is optionally provided to allow selection of different electrode configurations under the control of the microcontroller 20. The electrode configuration switch 26 may include multiple switches for connecting the desired electrodes to the appropriate I/O circuits, thereby facilitating electrode programmability. The switch 26 is controlled by a control signal 28 from the microcontroller 20. Optionally, the switch 26 may be omitted and the I/O circuits directly connected to a housing electrode.

The IMD 50 further includes a chamber pulse generator 22 that generates stimulation pulses for connecting the desired electrodes to the appropriate I/O circuits, thereby facilitating electrode programmability. The pulse generator 22 is controlled by the microcontroller 20 via control signals 24. The IMD 50 includes a sensing circuit 44 selectively coupled to one or more electrodes that perform sensing operations through the switch 26 to detect cardiac activity. The sensing circuit 44 may include dedicated sense amplifiers, multiplexed amplifiers, or shared amplifiers. The sensing circuit 44 may operate in a unipolar sensing configuration or a bipolar sensing configuration. The output of the sensing circuit 44 is connected to the microcontroller 20 which, in turn, triggers, or inhibits the pulse generator 22 in response to the absence or presence of cardiac activity. The sensing circuit 44 receives a control signal 46 from the microcontroller 20 for purposes of controlling the gain, threshold, polarization, and timing of any blocking circuitry (not shown) coupled to the sensing circuit.

The IMD 50 further includes an analog-to-digital ND data acquisition system (DAS) 84 coupled to one or more electrodes via the switch 26 to sample cardiac signals across any pair of desired electrodes. The A/D DAS 84 is controlled by a control signal 86 from the microcontroller 20.

The IMD 50 is communicatively connected to an external device 90. The external device 90 may represent the external device 16 in FIG. 1. The external device 90 may communicate with a telemetry circuit 64 of the IMD 50 through a communication link 66. The external device 90 facilitates access by physicians to patient data as well as permitting the physician to review real-time cardiac signals while collected by the IMD 50.

The microcontroller 20 is coupled to a memory 88 by a suitable data/address bus 62. The memory 88 stores the programmable operating parameters used by the microcontroller 20 and/or data associated with the detection and determination of arrhythmias.

The IMD 50 may further include one or more physiologic sensors 70 adjust pacing stimulation rates, detect changes in cardiac output, changes in the physiological condition of the heart, and/or diurnal changes in activity (e.g., detecting sleep and wake states). Examples of physiological sensors 70 might include sensors that, for example, sense respiration rate, pH of blood, ventricular gradient, activity, body movement, position/posture, minute ventilation (MV), and/or the like.

The battery 72 provides operating power to all of the components in the IMD 50. The battery 72 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more).

The IMD 50 further includes an impedance measuring circuit 74, which can be used for many things, including sensing respiration phase. The IMD 50 is further equipped with a communication modem (modulator/demodulator) 40 to enable wireless communication with the external device 90 and/or other external devices. The IMD 50 includes a shocking circuit 80 controlled by control signals 82 generated by the microcontroller 20. The shocking circuit 80 generates shocking pulses of low (e.g., up to 0.5 joules), moderate (e.g., 0.5-10 joules), or high energy (e.g., 11 to 40 joules), as controlled by the microcontroller 20.

The microcontroller 20 may include other dedicated circuitry and/or firmware/software components, such as a timing control (module) 32 and a morphology detector (module) 36. The timing control 32 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like. The morphology detector 36 is configured to review and analyze one or more features of the morphology of cardiac activity signals, such as the morphology of detected R waves to determine whether to include or exclude one or more beats from further analysis.

The embodiments described herein provide a corrosion-resistant feedthrough assembly that can be used for the manufacture of IMDs. The feedthrough assembly components provide protection against corrosion and other chemical and electrochemical reactions. One or more technical effects of the embodiments described herein include the ability to customize the feedthrough assembly by selecting from a variety of materials for the sealant and deposition techniques to tailor the non-corrosive sealant to a specific application (e.g., specific material compositions of the other components in the feedthrough assembly, specific configuration of the feedthrough assembly, etc.). Furthermore, the non-corrosive sealant can be applied to the feedthrough assembly without interfering with the manufacturing process. For example, the sealant can be applied after the feedthrough assembly is constructed, without requiring significant alterations to existing manufacturing processes or designs. The non-corrosive sealant provides added protection against unplanned anomalies with current neuromodulation and CRM device designs, such as anomalies that cause the loss of hermeticity of the device. The protection provided by the non-corrosive sealant also enables the development of feedthrough assemblies that can be designed for direct contact with body fluid and tissue. Such an ability may be beneficial for increased miniaturization of implantable medical devices.

Embodiments of the feedthrough assembly described herein may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

Additionally or alternatively, the IMD that includes the feedthrough assembly may be a leadless implantable medical device (LIMD). The LIMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the LIMD may be a leadless cardiac monitor (ICM) that includes one or more structural and/or functional aspects of the device(s) described in U.S. Patent Application having Docket No. A15E1059, U.S. patent application Ser. No. 15/084,373, filed Mar. 29, 2016, entitled, "Method And System To Discriminate Rhythm Patterns In Cardiac Activity," which is expressly incorporated herein by reference.

Additionally or alternatively, the IMD that includes the feedthrough assembly may be a subcutaneous IMD that includes one or more structural and/or functional aspects of the device(s) described in U.S. application Ser. No. 15/973, 195, titled "Subcutaneous Implantation Medical Device With Multiple Parasternal-Anterior Electrodes" and filed May 7, 2018, and U.S. application Ser. No. 15/973,219, titled "Implantable Medical Systems And Methods Including Pulse Generators And Leads" filed May 7, 2018, which are hereby incorporated by reference in their entireties. Further, one or more combinations of IMDs may be utilized from the above incorporated patents and applications in accordance with embodiments herein.

All references, including publications, patent applications and patents, cited herein are hereby incorporated by reference to the same extent as if each reference were individually and specifically indicated to be incorporated by reference and were set forth in its entirety herein.

It should be clearly understood that the various arrangements and processes broadly described and illustrated with respect to the figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A feedthrough assembly for an implantable medical device, the feedthrough assembly comprising:
   a housing including an inner surface that defines a central cavity through the housing, wherein the housing has a stepped top side including a horizontal ridge surface and a raised lip that define a well, the horizontal ridge surface radially extending from the inner surface of the housing to the raised lip, the raised lip projecting from the horizontal ridge surface to a top surface of the raised lip at a top end of the housing, wherein a continuous angled inner surface of the raised lip extends to the top surface of the raised lip so a cross-sectional area of the well continuously increases along the continuous angled inner surface with increasing proximity to the top surface of the raised lip;
   a solid insert disposed within the central cavity of the housing;
   one or more conductive elements extending through one or more apertures defined within the solid insert and extending through the central cavity of the housing, the one or more conductive elements including one or more wires or one or more pins;
   a metal filler disposed within a joint defined by an outer surface of the solid insert and the inner surface of the housing that defines the central cavity; and a non-corrosive sealant that covers a top surface of the solid insert and coats the metal filler to inhibit corrosion of the metal filler, wherein the non-corrosive sealant at least partially fills the well to cover the top surface of the solid insert and coat the metal filler, and a perimeter of the non-corrosive sealant conforms to the angled inner surface.

2. The feedthrough assembly of claim 1, wherein the non-corrosive sealant is electrically insulative.

3. The feedthrough assembly of claim 1, wherein the non-corrosive sealant comprises one or more of alumina, parylene, polyurethane, silicone, or an epoxy material.

4. The feedthrough assembly of claim 1, wherein the housing comprises a metal material and the solid insert comprises a ceramic material.

5. The feedthrough assembly of claim 1, wherein the housing comprises titanium.

6. The feedthrough assembly of claim 1, wherein the housing has protrusions along an outer perimeter of the housing configured to a header of the implantable medical device, and the one or more conductive elements are configured to electrically connect to at least one of an antenna or a sensing electrode held in the header.

7. The feedthrough assembly of claim 1, wherein the central cavity of the housing is elongated along an axis, and the one or more conductive elements include multiple conductive elements arranged in a line along the axis.

8. The feedthrough assembly of claim 1, wherein the metal filler comprises gold.

9. The feedthrough assembly of claim 1, wherein the metal filler is also disposed within the one or more apertures between the one or more conductive elements and the solid insert to seal the one or more apertures, and the non-corrosive sealant coats the top surface of the metal filler within the one or more apertures.

10. The feedthrough assembly of claim 1, wherein the non-corrosive sealant fills the well and coats at least a portion of the top surface of the raised lip at the top end of the housing.

11. The feedthrough assembly of claim 1, wherein the perimeter of the non-corrosive sealant conforms to the continuous angled inner surface to funnel the non-corrosive sealant towards the metal filler.

12. The feedthrough assembly of claim 1, wherein the cross-sectional area of the well that continuously increases along the continuous angled inner surface is a horizontal cross-section.

13. A method of producing a feedthrough assembly, the method comprising:

installing a solid insert within a central cavity of a housing, the central cavity extending through the housing and defined by an inner surface of the housing, wherein the housing has a stepped top side including a horizontal ridge surface and a raised lip that define a well, the horizontal ridge surface radially extending from the inner surface of the housing to the raised lip, the raised lip projecting from the horizontal ridge surface to a top surface of the raised lip at a top end of the housing, wherein a continuous angled inner surface of the raised lip extends to the top surface of the raised lip so a cross-sectional area of the well continuously increases along the continuous angled inner surface with increasing proximity to the top surface of the raised lip;

installing one or more conductive elements through one or more apertures defined within the solid insert, the one or more conductive elements including one or more wires or one or more pins;

depositing a metal filler within a joint defined by an outer surface of the solid insert and the inner surface of the housing that defines the central cavity; and forming a cover layer that covers a top surface of the solid insert and coats the metal filler, the cover layer composed of a non-corrosive sealant to inhibit corrosion of the metal filler, wherein forming the cover layer comprises at least partially filling the well with the non-corrosive sealant when in a flowable state so a perimeter of the non-corrosive sealant conforms to the angled inner surface.

14. The method of claim 13, wherein the cover layer is formed via one of chemical vapor deposition, physical vapor deposition, injection molding, precision fluid dispensing, or casting.

15. The method of claim 13, wherein the non-corrosive sealant comprises one or more of alumina, parylene, polyurethane, silicone, or an epoxy material, the solid insert comprises a ceramic material, and the housing comprises a metal material.

16. The method of claim 13, wherein forming the cover layer comprises filling the well with the non-corrosive sealant so that the non-corrosive sealant coats at least a portion of the top surface of the raised lip at the top end of the housing.

17. An implantable medical device comprising:

a header that comprises a header body, an antenna, and a sensing electrode, the antenna and the sensing electrode both disposed within the header body; and a feedthrough assembly mounted to a mounting end of the header body, the feedthrough assembly comprising:

a housing including an inner surface that defines a central cavity through the housing, wherein the housing has a stepped top side including a horizontal ridge surface and a raised lip that define a well, the horizontal ridge surface radially extending from the inner surface of the housing to the raised lip, the raised lip projecting from the horizontal ridge surface to a top surface of the raised lip at a top end of the housing, wherein a continuous angled inner surface of the raised lip extends to the top surface of the raised lip so a cross-sectional area of the well continuously increases along the continuous angled inner surface with increasing proximity to the top surface of the raised lip;

a solid insert disposed within the central cavity of the housing;

conductive elements extending through apertures defined within the solid insert and extending through the central cavity of the housing, the conductive elements including one or more of wires or pins, wherein a first conductive element of the conductive elements is electrically connected to the antenna and a second conductive element of the conductive elements is electrically connected to the sensing electrode;

a metal filler disposed within the apertures between the corresponding conductive elements and the solid insert to seal the apertures; and a non-corrosive sealant that fills the well and covers at least a portion of the top surface of the raised lip at the top end of the housing, the non-corrosive sealant forming a cover layer that covers a top surface of the solid insert and coats the metal filler to inhibit corrosion of the metal filler, wherein the header body couples to the housing of the feedthrough assembly and envelops the non-corrosive sealant.

18. The implantable medical device of claim 17, further comprising a case that encloses a battery and an electronics module within an internal cavity of the case, wherein the feedthrough assembly is disposed between the header and the case, and the conductive elements of the feedthrough assembly project into the internal cavity and electrically connect to the battery and the electronics module, and the feedthrough assembly maintains hermeticity of the case.

19. The implantable medical device of claim 17, wherein the metal filler is also disposed within a joint defined by an outer surface of the solid insert and the inner surface of the housing that defines the central cavity, and the non-corrosive sealant within the well covers the metal filler that is within the joint.

20. The implantable medical device of claim 17, wherein the continuous angled inner surface forms a lead-in surface to funnel the non-corrosive sealant towards the horizontal ridge surface, the metal filler, and the solid insert.

21. The implantable medical device of claim 17, wherein a perimeter edge of the non-corrosive sealant is defined by an inner surface of the raised lip extending from the horizontal ridge surface.

\* \* \* \* \*